(12) United States Patent
Tomura et al.

(10) Patent No.: US 7,803,411 B2
(45) Date of Patent: Sep. 28, 2010

(54) PHYSIOLOGICALLY ACTIVE SUBSTANCE NK13650P3, METHOD OF PRODUCING THE SAME AND USE THEREOF

(75) Inventors: Arihiro Tomura, Tokyo (JP); Junko Odanaka, Tokyo (JP); Masakazu Nishimoto, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 384 days.

(21) Appl. No.: 11/922,266

(22) PCT Filed: Jun. 26, 2006

(86) PCT No.: PCT/JP2006/312726
§ 371 (c)(1),
(2), (4) Date: Dec. 14, 2007

(87) PCT Pub. No.: WO2007/000978
PCT Pub. Date: Jan. 4, 2007

(65) Prior Publication Data
US 2009/0041799 A1 Feb. 12, 2009

(30) Foreign Application Priority Data
Jun. 27, 2005 (JP) .............................. 2005-186182

(51) Int. Cl.
*A61K 35/00* (2006.01)
*A01N 65/04* (2009.01)
*C12P 1/02* (2006.01)

(52) U.S. Cl. ........................ 424/780; 424/93.5; 435/171

(58) Field of Classification Search ........................ None
See application file for complete search history.

(56) References Cited

U.S. PATENT DOCUMENTS

| 4,221,705 | A | * | 9/1980 | Kondo | 530/329 |
| 4,368,193 | A | * | 1/1983 | Argoudelis et al. | 514/24 |
| 4,493,845 | A | * | 1/1985 | Omura et al. | 514/27 |
| 4,745,206 | A | * | 5/1988 | Bezoari | 558/80 |
| 4,935,543 | A | * | 6/1990 | Kanamaru et al. | 564/169 |
| 5,171,573 | A | * | 12/1992 | Suzuki et al. | 424/401 |
| 5,306,496 | A | * | 4/1994 | Morino et al. | 424/117 |
| 6,291,639 | B1 | * | 9/2001 | Conrad et al. | 530/329 |

FOREIGN PATENT DOCUMENTS

| EP | 0 722 940 | 7/1996 |
| JP | 7-206886 | 8/1995 |

OTHER PUBLICATIONS

Proksa et al. J. Antibiotics. Aug. 1992. vol. 45, No. 8, pp. 1268-1272.*
Kamal et al. Antonie van Leeuwenhoek. 2009. vol. 95, pp. 179-188.*
Clinical Oncology, 3rd Ed., Japanese Journal of Cancer and Chemotherapy, 2003, p. 256-260.
Clinical Oncology I. Principles of Oncology, 2nd Ed., Japanese Journal of Cancer and Chemotherapy, 1999, p. 63-72 with Partial English translation.
International Search Report dated Jul. 18, 2006.

* cited by examiner

*Primary Examiner*—Christopher R. Tate
(74) *Attorney, Agent, or Firm*—Nields, Lemack & Frame, LLC

(57) ABSTRACT

A physiologically active substance NK13650P3 having the following physicochemical properties or a pharmacologically acceptable salt thereof. 1) Appearance: pale yellow powder 2) Molecular formula: $C_{29}H_{37}N_7O_{15}$ 3) Molecular weight: 723 4) Hydrogen nuclear magnetic resonance spectrum: spectrum measured at 600 MHz in heavy water contains the following signals: chemical shift value δ ppm: 7.05 (1H, 3), 7.00 (1H, d), 6.96 (1H, d), 6.83 (1H, s), etc. 5) Carbon nuclear magnetic resonance spectrum: spectrum measured at 150 MHz in heavy water contains the following signals: chemical shift value δ ppm: 181.5(s), 181.4(s), 179.9(s), 179.2(s), 174.5(s), 174.3(s), 171.5(s), 165.4(s), etc. 6) Ultraviolet light spectrum: spectrum measured in aqueous solution contains the following UV absorption bands: $\lambda^{max}$ (MeOH): 196.5 nm, 224.5 nm, 322.5 nm 7) Solubility: highly soluble in water but insoluble in methanol, acetone, ethyl acetate, chloroform and dimethyl sulfoxide. 8) Coloration reaction: positive to phosphomolybdic acid/sulfuric acid reaction and Rydon-Smith reaction.

6 Claims, 3 Drawing Sheets

PHYSIOLOGICALLY ACTIVE SUBSTANCE NK13650P3, METHOD OF PRODUCING THE SAME AND USE THEREOF

TECHNICAL FIELD

The present invention relates to a physiologically active substance NK13650P3, a process for producing the same, and use thereof. The compound of the present invention inhibits cell growth and is expected as an anticancer substance used as a therapeutic drug or the like for a malignant tumor.

BACKGROUND ART

According to Non-Patent Document 1, anthracycline (e.g., doxorubicin), actinomycin, anthraquinone, mitomycin, bleomycin, neocarzinostatin, and chromomycin antibiotics have been known as anticancer antibiotics.

Breast cancer or prostatic cancer is hormone-dependent cancer whose cell growth is promoted by hormone such as estrogen or androgen. Thus, antihormonal drugs are used for this cancer. However, the hormone dependent cancer develops hormone resistance against these drugs (Non-Patent Document 2).

Non-Patent Document 1: ed. by Japan Clinical Oncology Group, CLINICAL ONCOLOGY, 3rd. ed., Japanese Journal of Cancer and Chemotherapy, issued in 2003, p. 256 to 260

Non-Patent Document 2: ed. by Japan Clinical Oncology Group, CLINICAL ONCOLOGY I. Principles of oncology, 2nd ed., Japanese Journal of Cancer and Chemotherapy, issued in 1999, p. 63 to 72

DISCLOSURE OF THE INVENTION

Conventional anticancer antibiotics are strongly toxic, therefore, they respond insufficiently. They have anticipated a novel compound which does not cause resistance.

Alternatively, an invention of a novel drug for hormone-dependent cancer has been desired.

The present inventors have investigated various microbial metabolites and have consequently found that one strain belonging to imperfect fungi produces a physiologically active substance NK13650P3 having cell growth inhibitory activity against mammal cancer cells, and that the NK13650P3 and a pharmacologically acceptable salt thereof have cell growth inhibitory activity against the cancer cells. The present inventors have conducted diligent studies on the basis of these findings and have consequently completed the present invention.

Specifically, the present invention relates to:

(1) a physiologically active substance NK13650P3 having the following physicochemical properties or a pharmacologically acceptable salt thereof:

1) colour and shape: pale yellow powder;
2) molecular formula: $C_{29}H_{37}N_7O_{15}$;
3) molecular weight: 723;
4) hydrogen nuclear magnetic resonance spectrum: a spectrum measured at 600 MHz in heavy water is as follows: chemical shift value δppm: 7.05 (1H, s), 7.00 (1H, d), 6.96 (1H, d), 6.83 (1H, s), 4.43-4.48 (2H, m), 4.28 (1H, m), 4.15 (2H, m), 3.21 (2H, m), 2.58-2.78 (6H, m), 2.34 (1H, m), 2.18 (1H, m), 1.99 (1H, m), 1.88 (1H, m), 1.71 (1H, m), 1.63 (1H, m)
5) carbon nuclear magnetic resonance spectrum: a spectrum measured at 150 MHz in heavy water is as follows: chemical shift value δppm: 181.5(s), 181.4(s), 179.9(s), 179.2(s), 174.5(s), 174.3(s), 171.5(s), 165.4(s), 159.7(s), 149.5(s), 149.2(s), 127.8(s), 126.2(d), 126.1(s), 122.0(d), 119.0(d), 117.1(d), 77.7(s), 68.8(t), 57.8(d), 55.1(d), 54.2(d), 47.4(t), 47.0(t), 43.4(t), 40.7(t), 34.2(t), 33.9(t), 25.9(t)
6) ultraviolet radiation spectrum: a spectrum measured in an aqueous solution is as follows:
$\lambda^{max}$ (MeOH): 196.5 nm, 224.5 nm, and 322.5 nm;
7) solubility: easily soluble to water and insoluble to methanol, acetone, ethyl acetate, chloroform, and dimethyl sulfoxide; and
8) color reaction: positive for phosphomolybdic acid-sulfuric acid and Rydon-Smith reagent;

(2) a pharmaceutical agent comprising a physiologically active substance NK13650P3 or a pharmacologically acceptable salt thereof according to (1);

(3) an antitumor agent comprising a physiologically active substance NK13650P3 or a pharmacologically acceptable salt thereof according to (1);

(4) a therapeutic agent for hormone-dependent cancer comprising a physiologically active substance NK13650P3 or a pharmacologically acceptable salt thereof according to (1);

(5) a process for producing a physiologically active substance NK13650P3 comprising: culturing, in a nutrient medium, a microbe belonging to genus *Penicillium* having an ability to produce a physiologically active substance NK13650P3 according to (1); allowing the microbe to produce and accumulate the physiologically active substance NK13650P3 into the cultures; and collecting this physiologically active substance NK13650P3;

(6) imperfect fungi of genus *Penicillium* having an ability to produce a physiologically active substance NK13650P3 according to (1); and (7) *Penicillium* sp. NF 13650 (deposition No.: FERM BP-10600) or a variant thereof.

The present invention provides a physiologically active substance NK13650P3 that has cell growth inhibitory activity, or a pharmacologically acceptable salt thereof. Conventional anticancer antibiotics are strongly toxic and respond insufficiently. By contrast, the novel compound of the present invention obtained from a microbial metabolite can be used as a satisfactory therapeutic drug for a malignant tumor. The novel compound of the present invention particularly has antitumor effects on hormone-dependent cancer and as such, can be used as a novel therapeutic agent for hormone-dependent cancer.

BEST MODE FOR CARRYING OUT THE INVENTION

Figure 1:
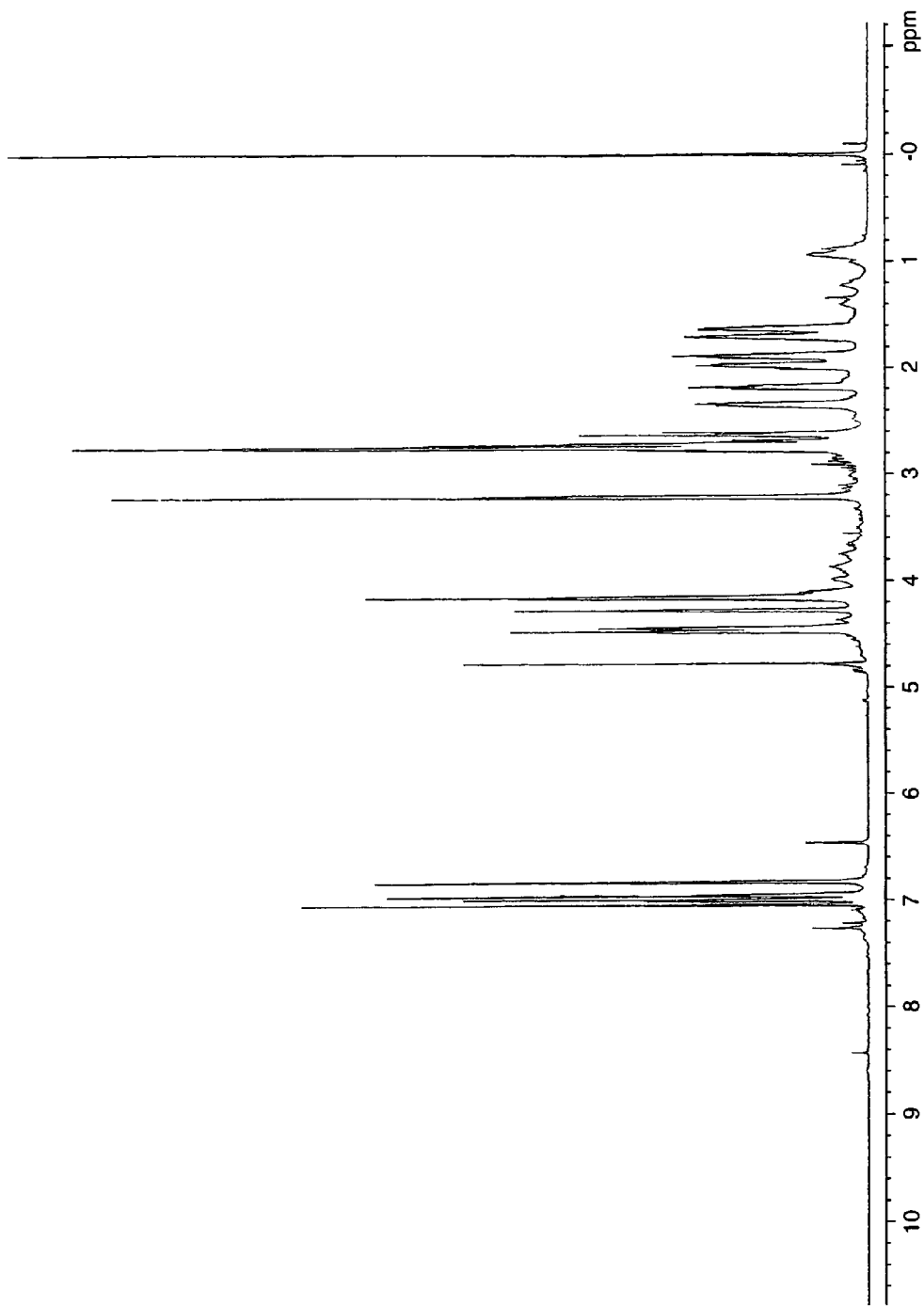
FIG. 1 shows a 600 MHz hydrogen nuclear magnetic resonance spectrum of NK13650P3 measured in heavy water.

Hereinafter, the present invention is described in detail.

A physiologically active substance NK13650P3 of the present invention is obtained by culturing its production strain belonging to genus *Penicillium*, allowing the strain to produce the compound, and collecting the compound from the cultures.

Typical examples of the NK13650P3 production strain include *Penicillium* sp. NF 13650 (deposition No.: FERM BP-10600) separated from soil. Hereinafter, the mycological properties of this strain are shown.

1. Morphological Characteristics

After 1 week of subculture at 25° C., the hyphae were formed on agar surface or in agar. The formation of colorless septate hyphae was observed. The conidiophores were unbranched or, on rare occasion, regularly branched. Metulae were formed at the tip of the conidiophores. A needle-like shape phialide, i.e. a conidiogenous cell, was formed at the tip of the metulae. The conidiophores, the metulae and the phialide form Bicyclic penicillus. The conidiospores were phialoconidia, which were formed in chains from the phialide and each consisted of single cell, and were ovoid or elliptical in shape having smooth or warty surface. Teleomorph formation could not be observed in long-term culture.

2. Growth in Various Mediums

The states of growth 1 week after subculture at 25° C. in various mediums are shown in Table 1 below.

TABLE 1

| Medium | Diameter of colony (mm) | Color tone | Surface texture | Soluble dye |
|---|---|---|---|---|
| Potato dextrose agar medium | 18-20 | Front: dark green<br>Back: orange to white | Velvet-like | Absent |
| 2% malt agar medium | 16-18 | Front: subdued green to sage green<br>Back: olive yellow to orange | Velvet-like | Absent |
| Oatmeal agar medium | 18-22 | Front: dark green<br>Back: olive yellow to orange | Velvet-like | Absent |
| Miura medium (LCA) | 16-18 | subdued green | Velvet-like | Absent |

On the basis of the observed morphological characteristics, a taxon up to genus name to which this strain belongs was presumed according to microbial strains described in Arx (1981), Barron (1968), Domsch et al. (1993a, b), and Kiffer and Morelet (2000). As a result, this strain was identified as one of imperfect fungi because it forms septate hyphae and no sexual reproductive organ. Furthermore, this strain was shown to belong to genus *Penicillium* among imperfect fungi, from such morphological characteristics that it forms green colonies, broom-like penicillus and colorless unicellular phialoconidia. Accordingly, this strain was designated as *Penicillium* sp. NF 13650.

The strain was domestically deposited as deposition No. FERM P-20505 on Apr. 14, 2005 with the international depositary authority International Patent Organism Depositary, National Institute of Advanced Industrial Science and Technology (Tsukuba Central 6, 1-1-1 Higashi, Ibaraki, Japan (zip code: 305-8566)) and internationally deposited as deposition No. FERM BP-10600 on Apr. 27, 2006 under the Budapest treaty.

The strain belonging to genus *Penicillium* that is used in the present invention has variable properties, as with other strains of genus *Penicillium*. The strain can be easily varied by artificial mutagenesis means using, for example, ultraviolet rays, X-rays, and reagents. Every and any variant thus obtained can be used in the present invention as long as it has an ability to produce the physiologically active substance NK13650P3 intended by the present invention.

To prepare the physiologically active substance NK13650P3 by a production process of the present invention, the strain is first cultured in an aerobic manner in a medium containing nutrients available by imperfect fungi. Nutrition sources known in the art and conventionally used in the culture of imperfect fungi can be used in the present invention. For example, glucose, glycerin, galactose, starch syrup, dextrin, sucrose, starch, molasses, and animal or plant oil can be used as carbon sources. Alternatively, for example, soybean meal, wheat, wheat germ, corn steep liquor, meat extracts, peptone, yeast extracts, ammonium sulfate, sodium nitrate, and urea can be used alone or in combination as nitrogen sources. In addition, it is also effective to add sodium, cobalt, chlorine, sulfuric acid, phosphoric acid, and inorganic salts capable of forming other ions to the medium, as required. Moreover, organic and inorganic matters that help the growth of the strain and promote the production of the physiologically active substance NK13650P3 can be added appropriately thereto.

A suitable culture method is a liquid culture method, particularly, a deep stirring culture method. An appropriate culture temperature is 15 to 37° C. In most cases, the culture is carried out at around 25 to 30° C. Though it varies depending on medium and culturing condition employed, the accumulation of the physiologically active substance NK13650P3 usually reaches its maximum after 1 to 10 days in both shake culture and tank culture. The culture is completed when the amount of the physiologically active substance NK13650P3 in the cultures reaches a peak. And the substance is isolated from the culture broth.

The physiologically active substance NK13650P3 can be extracted and purified from the culture broth, making use of its properties and usual separation means, appropriately. For details, the culture broth is centrifuged or filtered to separate a filtrate from the microbial cells. The filtrate is charged onto a cation-exchange resin DOWEX 50W×4 (trade name; manufactured by Dow Chemical Company) or the like and chromatographed using ammonia water or the like to obtain a fraction of the physiologically active substance NK13650P3.

In addition to the above-described method, other usual purification means, for example, adsorption chromatography, gel filtration chromatography, scraping from thin layer chromatography, and high-performance liquid chromatography, can be combined appropriately or performed repetitively to purify the physiologically active substance NK13650P3.

Figure 2:
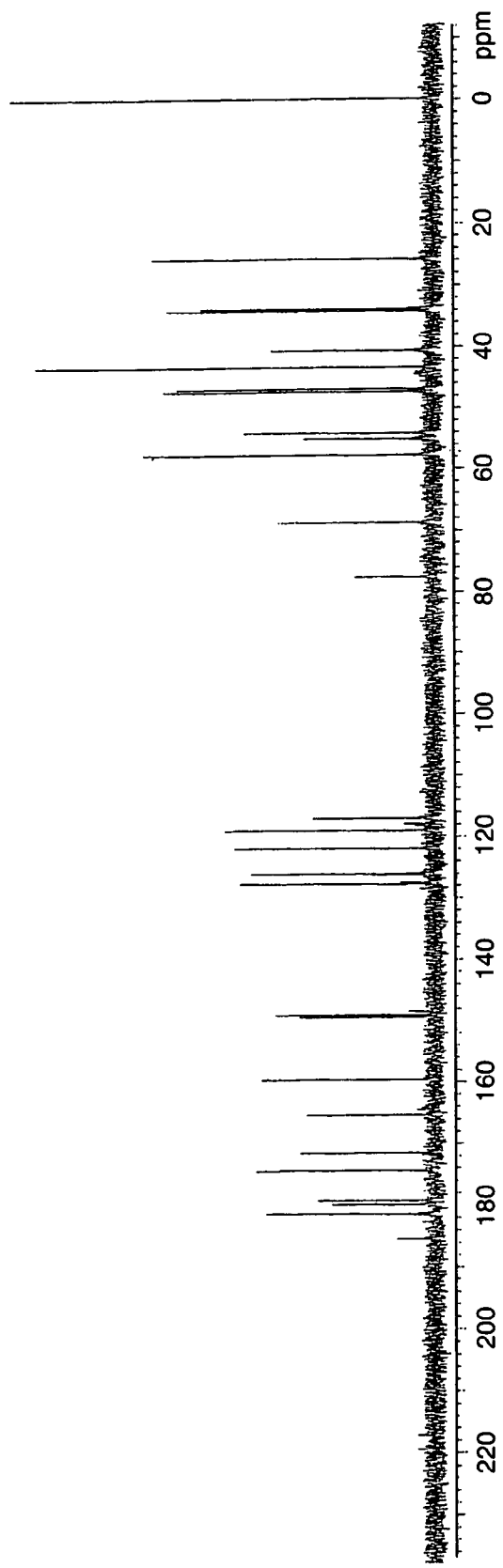
FIG. 2 shows a 150 MHz carbon nuclear magnetic resonance spectrum of NK13650P3 measured in heavy water.

The physicochemical properties of the physiologically active substance NK13650P3 thus obtained are shown below:

1) colour and shape: pale yellow powder;

2) molecular formula: $C_{29}H_{37}N_7O_{15}$;

3) molecular weight: 723 ($[M+H]^+$=724.24207 measured by an ESI method);

4) hydrogen nuclear magnetic resonance spectrum: a spectrum measured at 600 MHz in heavy water is shown in FIG. 1. The following signals are observed as characteristic signals:

chemical shift value δppm: 7.05 (1H, s), 7.00 (1H, d), 6.96 (1H, d), 6.83 (1H, s), 4.43-4.48 (2H, m), 4.28 (1H, m), 4.15 (2H, m), 3.21 (2H, m), 2.58-2.78 (6H, m), 2.34 (1H, m), 2.18 (1H, m), 1.99 (1H, m), 1.88 (1H, m), 1.71 (1H, m), 1.63 (1H, m), 5) carbon nuclear magnetic resonance spectrum: a spectrum measured at 150 MHz in heavy water is shown in FIG. 2. The following signals are observed as characteristic signals:

chemical shift value δppm: 181.5(s), 181.4(s), 179.9(s), 179.2(s), 174.5(s), 174.3(s), 171.5(s), 165.4(s), 159.7(s), 149.5(s), 149.2(s), 127.8(s), 126.2(d), 126.1(s), 122.0(d), 119.0(d), 117.1(d), 77.7(s), 68.8(t), 57.8(d), 55.1(d), 54.2(d), 47.4(t), 47.0(t), 43.4(t), 40.7(t), 34.2(t), 33.9(t), 25.9(t)

Figure 3:
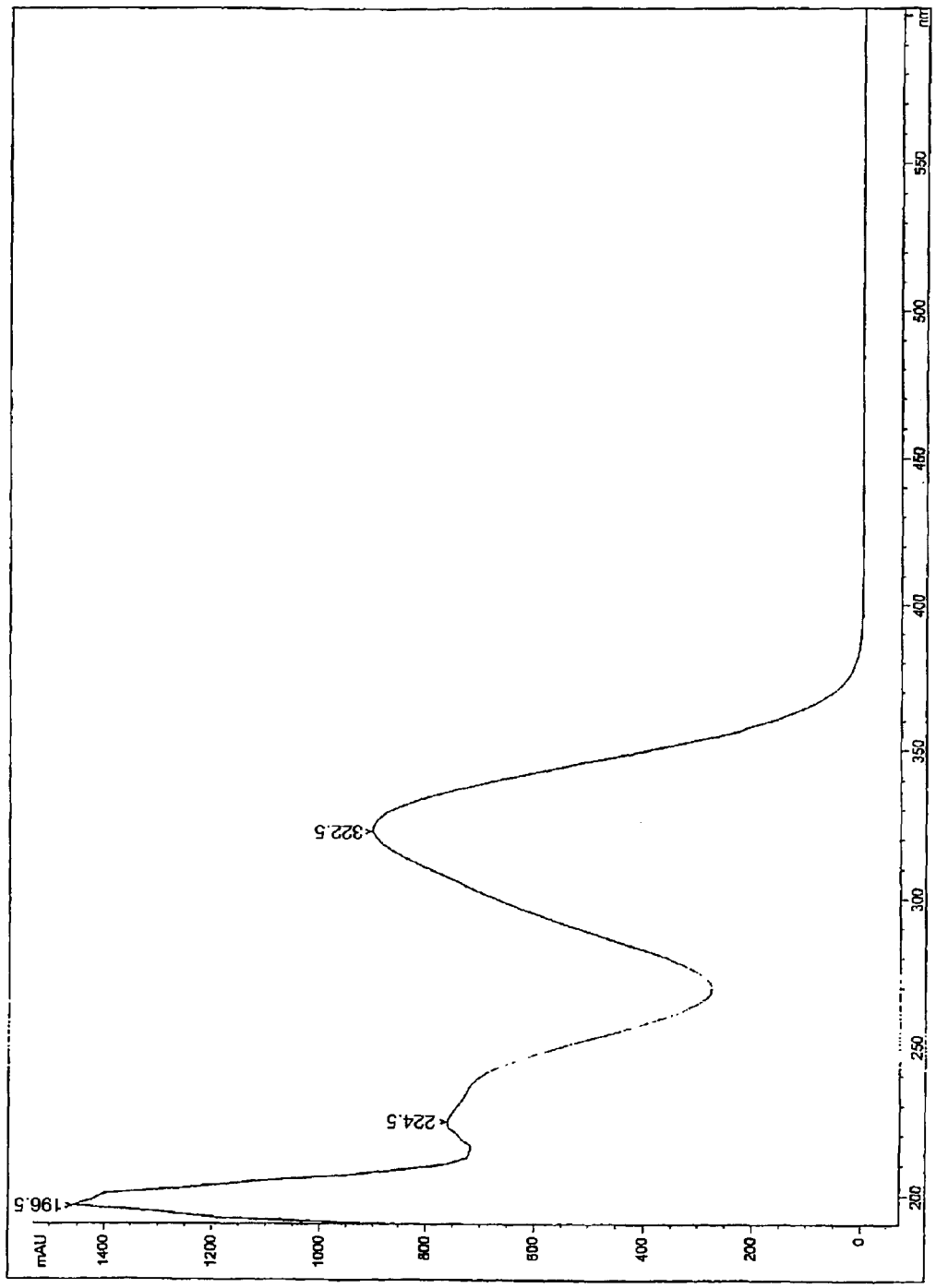
FIG. 3 shows an ultraviolet radiation spectrum measured in an aqueous solution of NK13650P3.

6) ultraviolet radiation spectrum: a spectrum measured in an aqueous solution is shown in FIG. 3. The following bands are observed as characteristic UV absorption bands:

$\lambda^{max}$ (MeOH): 196.5 nm, 224.5 nm, and 322.5 nm;

7) solubility: easily soluble to water and insoluble to methanol, acetone, ethyl acetate, chloroform, and dimethyl sulfoxide; and 8) color reaction: positive to phosphomolybdic acid-sulfuric acid and Rydon-Smith reagent.

In the present invention, a pharmacologically acceptable salt may be any of salts capable of being usually pharmacologically ingested and is, preferably, a salt with alkali, that is, a sodium salt, a potassium salt, or the like.

A variety of forms and methods conventionally known in the art can be applied to the dosage form and administration method of the physiologically active substance NK13650P3 or the pharmacologically acceptable salt thereof used as a pharmaceutical agent. The administration method may be, for example, injection, oral, or rectal administration. The dosage form may be, for example, any form of injections, powders, granules, tablets, suppositories, and capsules.

In a formulation, a variety of pharmaceutical additives used in pharmaceutical agents, that is, carriers and other aids, for example, stabilizers, preservatives, soothing agents, and emulsifiers, may be used as required, as long as they do not adversely affect the physiologically active substance NK13650P3 or the pharmacologically acceptable salt thereof. In the formulation, the content of the physiologically active substance NK13650P3 or the pharmacologically acceptable salt thereof may be changed in a wide range depending on dosage forms and so on. The content is generally 0.01 to 100% by weight, preferably, 0.1 to 70% by weight. The remaining portion is occupied by, as required, the additives usually used in pharmaceutical agents.

The dose of the physiologically active substance NK13650P3 or the pharmacologically acceptable salt thereof varies depending on conditions, administration methods, and so on. The dose in adult is approximately 0.01 to 800 mg/day.

EXAMPLES

Hereinafter, the present invention is described in further detail with reference to Examples.

Example 1

The preparation of a physiologically active substance NK13650P3 by a fermentation process is described.

(1) Fermentation

A seed culture medium comprising 3.0% soluble starch, 2.0% glucose, 1.0% gluten meal, 0.2% yeast extract (manufactured by Difco), 1.0% soybean meal (Sun Rich, manufactured by Showa Sangyo Co., Ltd.), 0.05% potassium dihydrogen phosphate, 0.05% magnesium sulfate, 0.1% potassium chloride, 0.00011% iron sulfate, 0.00064% copper sulfate, 0.00015% manganese chloride, 0.00079% zinc sulfate, 0.0001% cobalt chloride, and 0.01% PRONAL, was used. The medium before sterilization was adjusted to pH 6.7 for use.

100 mL of the medium in 500-mL Erlenmeyer flasks was sterilized at 120° C. for 20 minutes. 1 mL of frozen strains of *Penicillium* sp. NF 13650 was inoculated into the medium and cultured with a rotating shaker at 200 rpm at 30° C. for 2 days. The obtained strains were used as seeds.

A medium comprising 8.0% sucrose, 0.5% soybean meal (Sun Rich, manufactured by Showa Sangyo Co., Ltd.), 1.5% gluten meal, 0.2% yeast extract (manufactured by Difco), 0.05% magnesium sulfate, 0.1% potassium chloride, 0.00011% iron sulfate, 0.00064% copper sulfate, 0.00015% manganese chloride, 0.00079% zinc sulfate, 0.0001% cobalt chloride, and 0.01% PRONAL, was used. The medium before sterilization was adjusted to pH 6.7 for use. The medium was sterilized and then prepared by adding separately sterilized arginine and asparagine at each final concentration of 5 mg/mL.

The seeds were transferred in an inoculated amount of 1% to each of four hundred 500-mL Erlenmeyer flasks each containing 50 mL of the medium and cultured for 7 days. After the completion of culture, the culture broth was adjusted to pH 6.8 by the addition of 6 N sodium hydroxide. Then, the culture broth was centrifuged and further filtered to obtain 21 L of filtrate containing a physiologically active substance NK13650P3.

(2) Isolation

This filtrate was charged onto a cation-exchange resin DOWEX 50W×4 (manufactured by Dow Chemical Company; hydrogen ion type) and chromatographed using 2.8% ammonia water as a developing solvent. The obtained fraction was concentrated and freeze-dried to obtain 89.5 g of dark brown powder containing the physiologically active substance NK13650P3.

44 g of the dark brown powder containing the physiologically active substance NK13650P3 was dissolved in water. Then, the solution was charged to a G-10 column (1300-mL, φ4.0×100 cm, manufactured by GE Healthcare) filled in advance with water, then chromatographed using 2.0 L of water as a developing solvent. Of the obtained fractions, the fraction rich in the physiologically active substance NK13650P3 was concentrated and freeze-dried to obtain 38.7 g of fraction. The remaining 45.5 g of the freeze-dried product was also dissolved in water. Then, the solution was charged to a G-10 column (1300-mL, φ4.0×100 cm, manufactured by Merck Ltd. GE Healthcare) filled in advance with water, then chromatographed using 2.0 L of water as a developing solvent. Of the obtained fractions, the fraction rich in the physiologically active substance NK13650P3 was concentrated and freeze-dried to obtain 39.3 g of dark brown powder).

The physiologically active substance NK13650P3-containing freeze-dried products (38.7 g and 39.3 g) obtained in the first and second runs of G-10 column chromatography, respectively, were separately dissolved in water. Then, each of the solutions was charged to a 600-mL medium-pressure silica gel column (Silica Gel 60, φ5.0×30 cm, manufactured by Merck Ltd.), which was filled with silica gel by a dry process, deaerated with ethanol, and washed with water in advance. 900 mL of water and 900 mL of 50% aqueous ethanol were charged thereto. Then, the dark brown powder was chromatographed using 3 L of mixed solvent of ethanol: 28% aqueous ammonia:water=7:1:2 as a developing solvent.

The first and second fractions rich in the physiologically active substance NK13650P3 were together concentrated and freeze-dried to obtain 29.7 g of brown powder.

Subsequently, this 29.7 g of the brown powder containing the physiologically active substance NK13650P3 was purified in three portions by medium-pressure column chromatography under the same conditions. Specifically, in the first purification, 10.1 g of 15 mL aqueous solution was charged to a reverse-phase column (PEGASIL PREP ODS-5015-12A, $\phi 5.0 \times 35$ cm, manufactured by Senshu Scientific Co., Ltd.). The column was washed with 800 mL of water. Then, 800 mL of 4.5% methanol/aqueous solution of 10 mM ammonium acetate was charged thereto. The physiologically active substance NK13650P3 was chromatographed using 4.0 L of 10% methanol/aqueous solution of 10 mM ammonium acetate as a developing solvent. The second purification (9.5 g/15 mL) and the third purification (10.1 g/15 mL) were performed in the same way. Of the eluted fractions from these three purifications, the fraction rich in the physiologically active substance NK13650P3 was concentrated to obtain 12 g of yellow powder containing a salt.

This 12 g of the yellow powder containing a salt was dissolved in 5 mL of water. The solution was charged to a G-10 column (1300-mL, $\phi 4.0 \times 100$ cm) filled in advance with water. The column was developed, followed by desalting. The desalted fraction rich in the physiologically active substance NK13650P3 was concentrated and freeze-dried to obtain 1.3 g of yellow powder.

This 1.3 g of the yellow powder was purified by medium-pressure column chromatography. For details, 5 mL of aqueous solution was charged to a reverse-phase column (PEGASIL PREP ODS-5015-12A, $\phi 3.5 \times 35$ cm, manufactured by Senshu Scientific Co., Ltd.). The yellow powder was chromatographed with a linear gradient of 1000 mL of 4.5% methanol/aqueous solution of 10 mM ammonium acetate and 1000 mL of 10% methanol/aqueous solution of 10 mM ammonium acetate. Of the eluted fractions, the fraction rich in the physiologically active substance NK13650P3 was concentrated to obtain 490 mg of pale yellow powder containing a salt.

This 490 mg of the pale yellow powder was dissolved in an aqueous solution of 10 mM ammonium acetate. The fraction rich in the physiologically active substance NK13650P3 was purified by reverse-phase high-performance liquid chromatography. For details, a reverse-phase column (PEGASIL ODS, $\phi 30 \times 250$ mm, manufactured by Senshu Scientific Co., Ltd.) was used and the powder was chromatographed using 4.5% methanol/aqueous solution of 10 mM ammonium acetate at a flow rate of 20 mL/min. for 80 minutes. The physiologically active substance NK13650P3 was eluted with retention time of 40 to 50 minutes. The fraction of the physiologically active substance NK13650P3 was concentrated after distillation for removing methanol.

The concentrate was brought up to 2 mL by the addition of water. A G-10 chromatographic column (630-mL, $\phi 3 \times 90$ cm) was used and developed with water. The obtained NK13650P3 fraction was freeze-dried to obtain 12 mg (pale yellow powder) of physiologically active substance NK13650P3.

The physiologically active substance NK13650P3 was positive to phosphomolybdic acid-sulfuric acid and Rydon-Smith reagent and negative to ninhydrin, Sakaguchi reaction, p-anisaldehyde, and ferric chloride in color reaction.

Example 2

An assay of the cell growth inhibitory activity of the physiologically active substance NK13650P3 against mammal cancer cells is described.

Test Example 1

Cell Growth Inhibitory Activity

Hormone-dependent human prostatic cancer cells LNCaP were maintained in a Daigo's T medium (manufactured by Wako Pure Chemical Industries, Ltd.) supplemented with 25% GIT medium (manufactured by Wako Pure Chemical Industries, Ltd.) at 37° C. under 5% $CO_2$. Alternatively, hormone-independent human prostatic cancer cells PC-3 were maintained in a D-MEM medium (Nikken Chemicals Co., Ltd.) at 37° C. under 5% $CO_2$. These cells were inoculated on a 96-well plate at a concentration of 2000 cells/well and cultured for 1 day. Then, the physiologically active substance NK13650P3 was added to the wells. For the LNCaP cells, dihydrotestosterone was added at a final concentration of 0.1 nM simultaneously with the physiologically active substance NK13650P3, and the cells were treated for 6 days. The number of cells was evaluated by a methylene blue method. 31.6 µg/mL of the substance NK13650P3 inhibited the growth of 47% of the LNCaP cells. On the other hand, 31.6 µg/mL of the substance NK13650P3 did not inhibit the growth of the PC3 cells.

Test Example 2

Cell Growth Inhibitory Activity

Human breast cancer cells T-47D were maintained at 37° C. under 5% $CO_2$ using a Daigo's T medium supplemented with 10% GF21 (manufactured by Wako Pure Chemical Industries, Ltd.). The cells were inoculated on a 96-well plate at a concentration of 2000 cells/well and cultured for 1 day. Then, the physiologically active substance NK13650P3 was added to the wells. β-estradiol was added at a final concentration of 0.1 nM simultaneously with the physiologically active substance NK13650P3, and the cells were treated for 6 days. The number of cells was evaluated by a methylene blue method. 20 µg/mL of the substance NK13650P3 inhibited the growth of 30% of the T-47D cells.

As can be seen from these Test Examples, the physiologically active substance NK13650P3 of the present invention inhibits the growth of mammal cancer cells. The physiologically active substance NK13650P3 of the present invention particularly inhibits the growth of hormone-dependent prostatic cancer cells and breast cancer cells.

INDUSTRIAL APPLICABILITY

A novel compound of the present invention obtained from a microbial metabolite can be used as a therapeutic drug for a malignant tumor. The novel compound of the present invention particularly has antitumor effects on hormonal-dependent cancer and as such, can be used as a novel therapeutic agent for hormone-dependent cancer.

The invention claimed is:

1. A physiologically active substance NK13650P3 having the following physicochemical properties or a pharmacologically acceptable salt thereof:
   1) colour and shape: pale yellow powder;
   2) molecular formula: $C_{29}H_{37}N_7O_{15}$;
   3) molecular weight: 723;
   4) hydrogen nuclear magnetic resonance spectrum: a spectrum measured at 600 MHz in heavy water is as follows: chemical shift value δppm: 7.05 (1H, s), 7.00 (1H, d), 6.96 (1H, d), 6.83 (1H, s), 4.43-4.48 (2H, m), 4.28 (1H, m), 4.15 (2H, m), 3.21 (2H, m), 2.58-2.78 (6H, m), 2.34 (1H, m), 2.18 (1H, m), 1.99 (1H, m), 1.88 (1H, m), 1.71 (1H, m), 1.63 (1H, m)
   5) carbon nuclear magnetic resonance spectrum: a spectrum measured at 150 MHz in heavy water is as follows: chemical shift value δppm: 181.5(s), 181.4(s), 179.9(s), 179.2(s), 174.5(s), 174.3(s), 171.5(s), 165.4(s), 159.7(s), 149.5(s), 149.2(s), 127.8(s), 126.2(d), 126.1(s), 122.0(d), 119.0(d), 117.1(d), 77.7(s), 68.8(t), 57.8(d), 55.1(d), 54.2(d), 47.4(t), 47.0(t), 43.4(t), 40.7(t), 34.2(t), 33.9(t), 25.9(t)
   6) ultraviolet radiation spectrum: a spectrum measured in an aqueous solution is as follows: $\lambda^{max}$ (MeOH): 196.5 nm, 224.5 nm, and 322.5 nm;
   7) solubility: easily soluble to water and insoluble to methanol, acetone, ethyl acetate, chloroform, and dimethyl sulfoxide; and
   8) color reaction: positive for phosphomolybdic acid-sulfuric acid and Rydon-Smith reagent.

2. A pharmaceutical agent comprising a physiologically active substance NK13650P3 or a pharmacologically acceptable salt thereof according to claim 1.

3. An antitumor agent comprising a physiologically active substance NK13650P3 or a pharmacologically acceptable salt thereof according to claim 1.

4. A therapeutic agent for hormone-dependent cancer comprising a physiologically active substance NK13650P3 or a pharmacologically acceptable salt thereof according to claim 1.

5. A process for producing a physiologically active substance NK13650P3, comprising: culturing, in a nutrient medium, a microbe belonging to *Penicillium* sp. NF 13650 and having an ability to produce a physiologically active substance NK13650P3 according to claim 1; allowing the microbe to produce and accumulate the physiologically active substance NK13650P3 into the cultures; and collecting this physiologically active substance NK13650P3.

6. A biologically pure culture of *Penicillium* sp. NF 13650 (deposition No: FERM BP-10600) or a variant thereof having the ability to produce the physiologically active substance NK 13650P3.

* * * * *